(12) United States Patent
Walsh

(10) Patent No.: US 6,490,880 B1
(45) Date of Patent: Dec. 10, 2002

(54) REGULATED ORGAN CONTAINMENT SHIPPING SYSTEM USING DUAL-LAYER PRESERVATION LIQUID

(75) Inventor: Stephen E Walsh, North Oaks, MN (US)

(73) Assignee: Islet Technology Inc., White Bear Lake, MN (US)

( * ) Notice: Subject to any disclaimer, the term of this patent is extended or adjusted under 35 U.S.C. 154(b) by 85 days.

(21) Appl. No.: 09/696,985

(22) Filed: Oct. 26, 2000

(51) Int. Cl.$^7$ ................................................ F25D 3/08
(52) U.S. Cl. ....................................... 62/457.9; 62/371
(58) Field of Search .............................. 62/306, 457.2, 62/457.9, 371, 463, 530, 186; 206/583; 217/52

(56) References Cited

U.S. PATENT DOCUMENTS

| | | | |
|---|---|---|---|
| 3,656,649 A | * | 4/1972 | Martin .......................... 217/52 |
| 3,738,914 A | * | 6/1973 | Thorne et al. .............. 195/127 |
| 3,777,507 A | | 12/1973 | Burton et al. |
| 3,810,867 A | | 5/1974 | Peterson |
| 3,881,990 A | | 5/1975 | Burton et al. |
| 3,995,444 A | | 12/1976 | Clark et al. |
| 4,292,817 A | | 10/1981 | Loucks |
| 4,424,687 A | | 1/1984 | Morgan |
| 4,473,637 A | | 9/1984 | Guibert |
| 4,475,759 A | | 10/1984 | Wine |
| 4,494,385 A | * | 1/1985 | Kuroaka et al. .............. 62/306 |
| 4,502,295 A | | 3/1985 | Toledo-Pereyra |
| 4,530,816 A | | 7/1985 | Douglas-Hamilton |
| 4,576,017 A | | 3/1986 | Combs et al. |
| 4,723,974 A | | 2/1988 | Ammerman |
| 4,951,482 A | | 8/1990 | Gilbert |
| 4,958,506 A | | 9/1990 | Guilhem et al. |
| 5,232,095 A | * | 8/1993 | Childers et al. ............ 206/583 |
| 5,285,657 A | | 2/1994 | Bacchi et al. |
| 5,326,706 A | * | 7/1994 | Yland et al. ................. 435/283 |
| 5,355,684 A | * | 10/1994 | Guice .......................... 62/54.2 |
| 5,434,045 A | | 7/1995 | Jost |
| 5,476,763 A | | 12/1995 | Bacchi et al. |
| 5,586,438 A | | 12/1996 | Fahy |
| 6,046,046 A | | 4/2000 | Hassanein |

FOREIGN PATENT DOCUMENTS

WO    WO 99/35453    7/1999

OTHER PUBLICATIONS

*A New, Simple Method for Cold Storage of the Pancreas Using Perfluorochemical*, Transplantation, vol. 46, No. 3, pp. 457–460, Sep. 1988.
*Excellence of Perfluorochemical With Simple Oxygen Bubbling as a Preservation Medium for Simple Cold Storage of Canine Pancreas*, Transplantation, vol. 49, No. 3, pp. 648–650, Mar. 1990.
*Mechanism of Oxygenation of Pancreas During Preservation By a Two–Layer (Euro–Collins' Solution/Perfluorochemical) Cold–Storage Method*, Transplantation, vol. 49, No. 4, pp. 694–696, Apr. 1990.

* cited by examiner

Primary Examiner—Denise L. Esquivel
Assistant Examiner—Melvin Jones
(74) Attorney, Agent, or Firm—Patterson, Thuente, Skaar & Christensen, P.A.

(57) ABSTRACT

An organ containment shipping system has an outer container adapted to receive a passive cooling medium and an inner container adapted to receive an organ to be transported in a preservation medium. The inner container is positioned within the outer container by structure that includes a gimbal mechanism to substantially maintain the inner container in a predefined orientation in the event of a change of orientation of the outer container. Preferably, the preservation medium is a dual-layer preservation liquid having a bottom oxygen carrying layer and a top layer and the inner container include a perforated plate positioned in the inner container above a level of the bottom layer to prevent the organ from rising in the preservation medium. In one embodiment, the organ containment shipping system includes a system for regulating a level of the preservation medium relative to the organ and a system for regulating a temperature of the organ relative to the cooling medium.

14 Claims, 8 Drawing Sheets

REGULATED ORGAN CONTAINMENT SHIPPING SYSTEM USING DUAL-LAYER PRESERVATION LIQUID

FIELD OF THE INVENTION

The present invention relates generally to the field of organ preservation or perfusion apparatus. More specifically, the present invention relates to a regulated organ containment shipping system that maintains the temperature and level of a dual-layer preservation liquid surrounding the organ during shipment without the need for perfusion or active refrigeration.

BACKGROUND OF THE INVENTION

The need to maintain organs and tissue in a viable and sterile condition until they can be transplanted is well known. Originally, organs and tissue were simply wrapped in surgical towels and packed in ice in an ice chest to be shipped from one location to another.

Various organ storage devices that utilize ice, ice water or dry ice as a passive coolant have been developed over the years. U.S. Pat. No. 3,810,867 describes a passive coolant dual container system having an organ holding container disposed in and bonded to another compartment that holds the ice and water coolant. U.S. Pat. No. 4,502,295 describes a passive coolant dual container system with multiple inner containers. U.S. Pat. No. 4,530,816 describes a passive coolant dual container system with an insulating sheet having a selected thermal transfer rate separating the ice from the inner container. U.S. Pat. No. 4,576,017 describes a passive dual container system that uses internal blocks and fins to separate the inner container from the dry ice that is used as the passive coolant. U.S. Pat. No. 4,951,482 describes a passive coolant dual container system similar to a thermos having an inner container for carrying an organ in a preservation medium where the inner container is held in a coaxial arrangement within an outer container that houses the cooling fluid. U.S. Pat. No. 4,958,506 describes a passive coolant dual container system in which a heat pump is used to transfer thermal energy between the inner container and the passive ice coolant in the outer container.

PCT Publ. WO 99/35453 describes a temperature regulated dual container passive coolant organ storage system. The system provides for temperature regulation by using air temperature sensors located around the outer container to control the operation of two battery-powered fans in the lid of the outer container. The fans circulate air over crushed ice in the bottom of the outer container which then cools a stainless steel inner container that houses the organ on a stand within the inner container. The organ is double bagged and placed on the stand. The inner container is then sealed and placed on a metal platform in the outer container for shipment. A microprocessor controls the operation of the system and records temperatures during shipment in an associated memory that are displayed on an electronic console on the outside of the lid of the device.

Other types of cooling systems have also been utilized in organ storage devices. For example, U.S. Pat. Nos. 4,292,817, 4,473,637, and 4,745,759 describe organ storage systems that utilize active refrigeration with a cooling liquid being pumped through the system. U.S. Pat. No. 4,723,974 describes a flexible membrane storage system for amputated members in which two chambers in the outer container with different chemicals create the desired cooling when the divider between the chambers is broken and the chemicals are mixed. U.S. Pat. No. 5,434,045 describes a dual container organ storage system in which the inner container is a sealed concave receptacle for the organ having a first airflow chamber that is put inside the outer container having a second airflow chamber and a fan powered by a micromotor that re-circulates a refrigerant gas through the airflow chambers to keep the system cool.

It is known that maintaining the organ or tissue in an oxygenated environment improves viability. U.S. Pat. Nos. 3,777,507, 3,881,990, 3,995,444, 5,285,657, 5,476,763, and 6,046,046 describe various types of organ storage systems that actively perfuse oxygen into a preservation liquid (such as UW solution) that is pumped around the organ. These active storage devices may also provide for a pumped refrigeration system. U.S. Pat. No. 5,586,438 describes an organ storage system that can utilize either passive/static cooling with cooled preservation solution or active refrigeration and perfusion by incorporating connections for active refrigeration and perfusion of the UW solution. While effective, these type of active organ storage devices are quite complicated and expensive due to the pumping systems that are required.

One type of preservation solution that was initially developed by Kuroda et al. of Kobe University School of Medicine is a dual-layer preservation solution. As described in *Transplantation*, Vol. 46, No. 3, September 1988, pp. 457–60, the dual-layer preservation solution utilizes a high oxygen carrier perflourochemical (PFC) liquid as a bottom layer with a Euro-Collins (EC) solution as a top layer. The organ floats in a container between the top and bottom layer and oxygen is actively perfused into the PFC bottom layer. The container is maintained at a cold storage condition by placing the container in an ice-water bath. Variations on this original configuration included not perfusing oxygen into the PFC bottom layer and floating the organ in the EC top layer. Kuroda et al., *Transplantation*, Vol. 49, No. 4, April 1990, pp. 694–96. Another variation involved using a wire net compressor to hold the organ down into the PFC bottom layer. Kuroda et al., *Transplantation*, Vol. 49, No. 3, March 1990, pp. 648–50.

While the dual-layer preservation solution has worked well in a laboratory or hospital environment for maintaining the viability of organs, little has been done to adapt a portable organ transport system to utilize this dual-layer preservation solution. Typically, a plastic container is used as the inner container of a passive coolant dual container storage system. The plastic container has a lid with a screw down grate that is used to hold the organ in the PFC bottom layer. This plastic container is then placed on a stand in an outer container that is a conventional ice chest with the bottom filled with crushed ice. Although this arrangement is satisfactory, it would be desirable to provide for an organ containment shipping system that was specifically adapted for use with a dual-layer preservation solution.

SUMMARY OF THE INVENTION

The present invention is an organ containment shipping system having an outer container adapted to receive a passive cooling medium and an inner container adapted to receive an organ to be transported in a preservation medium. The inner container is positioned within the outer container by structure that includes a gimbal mechanism to substantially maintain the inner container in a predefined orientation in the event of a change of orientation of the outer container. Preferably, the preservation medium is a dual-layer preservation liquid having a bottom oxygen carrying layer and a top layer. The inner container includes a perforated plate positioned in the inner container above a level of the bottom layer to prevent the organ from rising in the preservation medium.

In one embodiment, the organ containment shipping system includes a system for regulating a level of the preservation medium relative to the organ and a system for regulating a temperature of the organ relative to the cooling medium. Preferably, the system for regulating the level of the preservation medium includes an inlet port having an inlet tube extending into the inner container below the perforated plate and an outlet port defined in a top of the inner container such that the level of the bottom layer can be adjusted by introducing or withdrawing fluid for the bottom layer through the inlet port. Preferably, the system for regulating the temperature of the organ relative to the passive cooling medium includes at least one fan operably connected to an electronic module that houses at least one battery and circuitry. The circuitry is connected to at least one sensor that activate the fans when the sensor indicates that the temperature has risen above a first predetermined level and deactivates the fans when the sensor indicates that the temperature has fallen below a second predetermined level.

DETAILED DESCRIPTION OF THE PREFERRED EMBODIMENT

Figure 9:
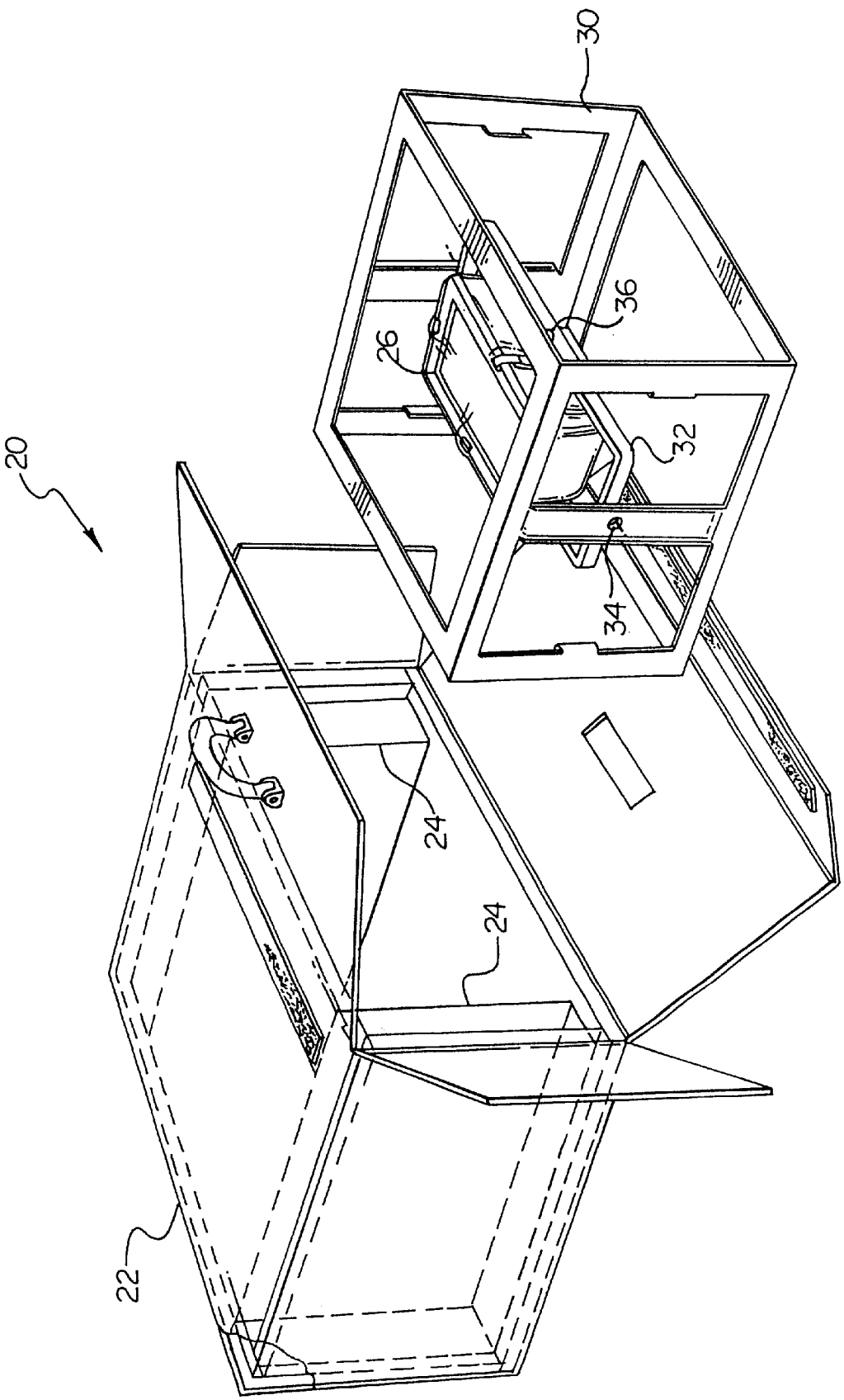
FIG. 9 is an exploded view showing the assembled main frame and the outer container.
Figure 13:
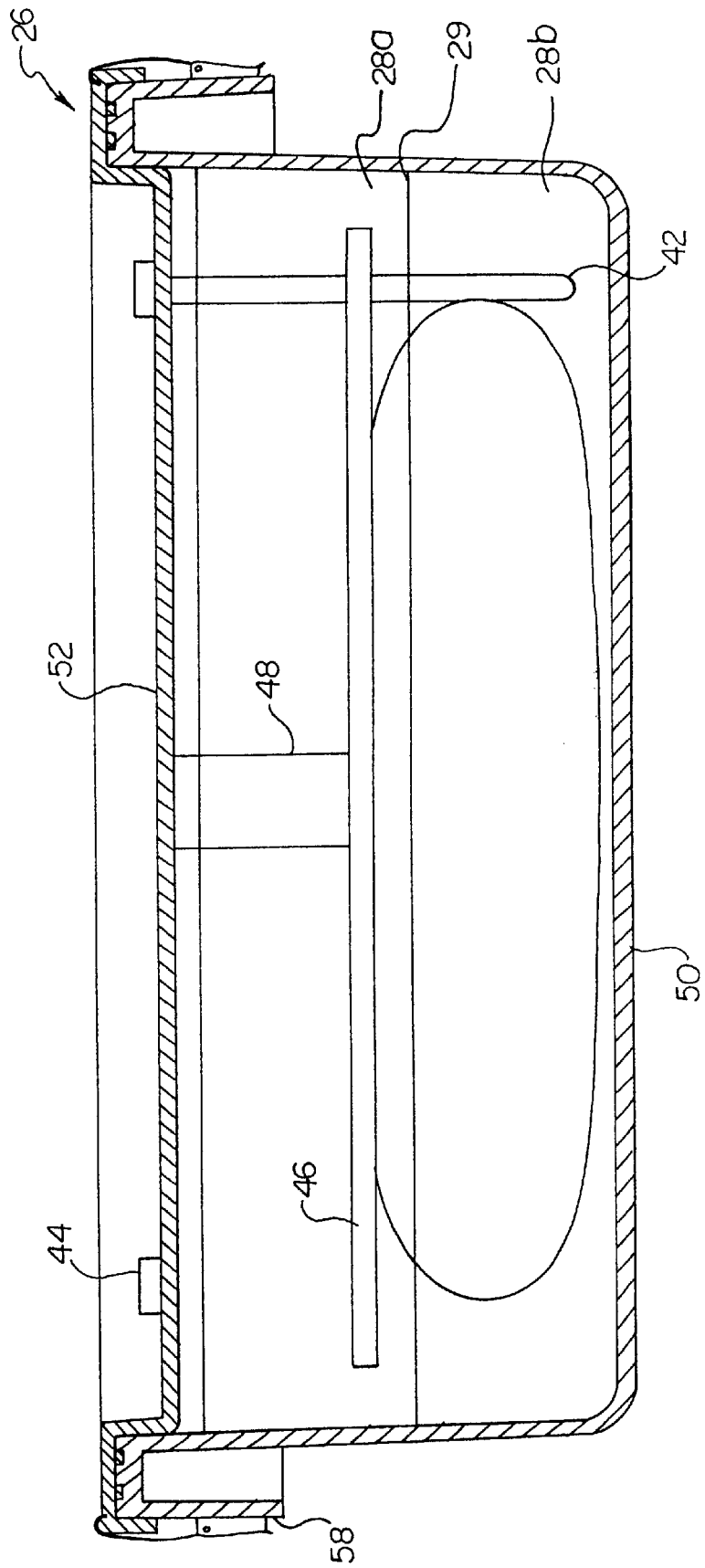
FIG. 13 is a side view of the organ tray showing an organ and a double-layer preservation fluid.

Referring to FIG. 9, a preferred embodiment of an organ containment shipping system 20 is shown in an exploded view with its various components. The organ containment shipping system includes an outer container 22 that is adapted to receive a passive cooling medium preferably in the form of cooling packs 24. An inner container 26 is adapted to receive an organ to be transported in a preservation medium 28 as shown in FIG. 13. In a preferred embodiment, a main gimbal frame 30 and inner gimbal frame 32 form a structure to position the inner container 26 within the outer container 22. The main gimbal frame 30 and secondary gimbal frame 32 are connected with a first pair of pivot assemblies 34 and second pair of pivot assemblies 36 to form a gimbal mechanism that substantially maintains the inner container 26 in a predefined orientation in the event of a change of orientation of the outer container 22.

Figure 1:
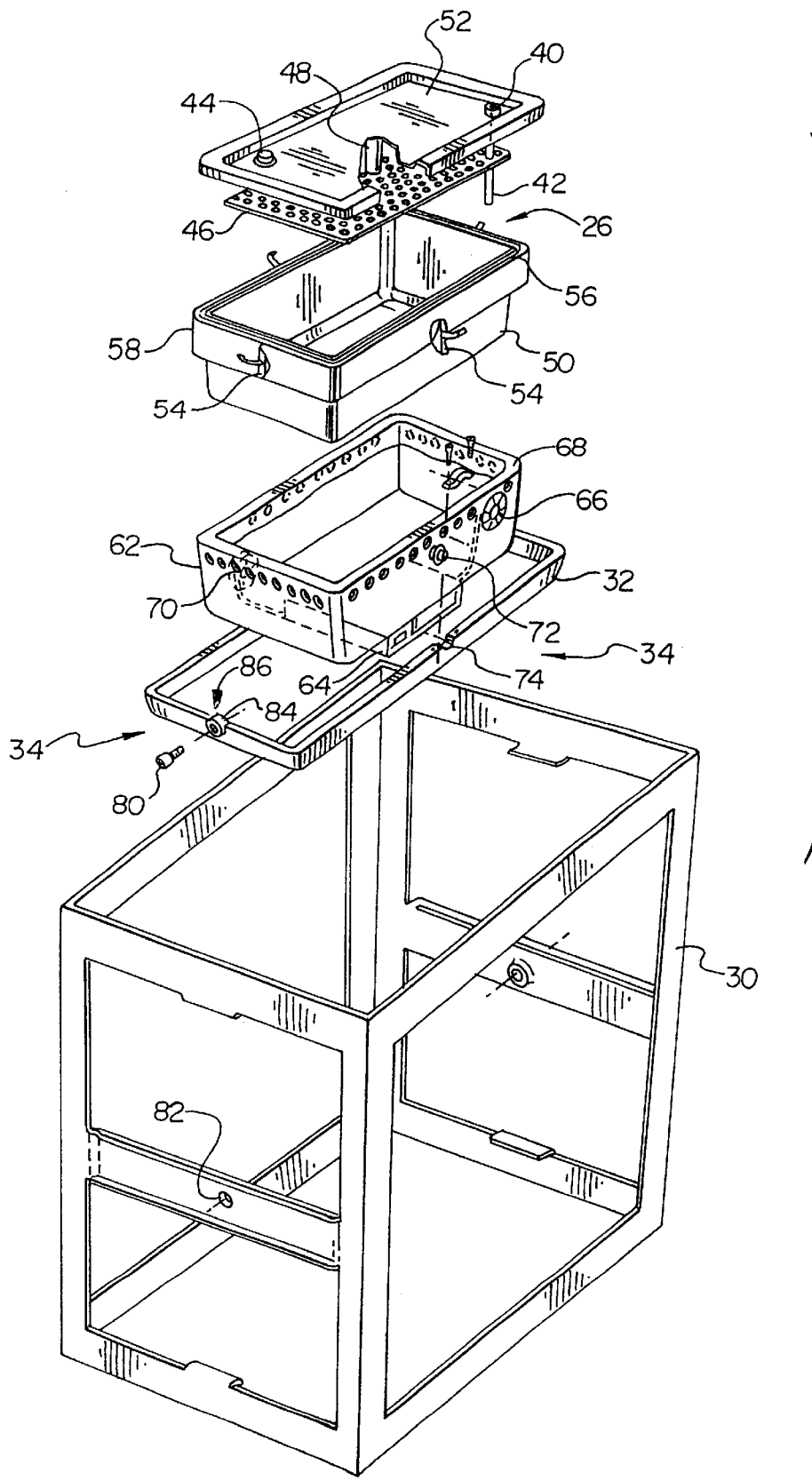
FIG. 1 is an exploded perspective view of the organ containment shipping system of the present invention with the main frame in a vertical orientation.

Referring now to FIG. 1, an inlet port 40 having an inlet tube 42 extending into the inner container 26 together with an outlet port 44 are utilized to adjust a level of the preservation medium 28. Preferably, the preservation medium 28 is a dual layer preservation medium such as described by Kuroda et al. The specific gravities of the layers 28a and 28b of the dual layer preservation medium 28 allow the organ to float in the dual layer preservation medium 28 as shown in FIG. 13. The organ is physically prevented from rising in the preservation medium 28 above a certain level by a perforated plate 46. The plate 46 is positioned at a predetermined level within the inner container 26 by a standoff structure 48. Preferably, the inner container 26 is comprised of a tray 50 and a cover 52. The standoff structure 48 is connected to the cover 52. The cover 52 is releasably attached to the tray 50 by a series of hinged clips 54. Preferably, the clips 54 are metal over-center latches that screw onto the tray 50 and mate with a metal insert in the cover 52. An O-ring 56 is positioned in a collar structure 58 defined around a top periphery of the tray 50 to seal the contents inside when the cover 52 is attached to the tray 50. It will be recognized that a wide variety of latching and sealing mechanisms could be used, such as a hinged cover, mechanisms internal or external to the tray 50, collars, straps, fasteners, slot and grove arrangements, friction fit or the like.

Preferably, the tray 50 is formed of a clear medical grade plastic to allow for observation of the organ and the preservation medium 28. The cover 52, standoff structure 48 and perforated plate 46 may also be formed of a medical grade plastic material. Alternatively, the cover 52, standoff structure 48 and perforated plate 46 may be made of metal. The standoff structure 48 may comprise one or more fixed length posts attached between the perforated plate 46 and the cover 52. Alternatively, the standoff structure 48 could include a mechanism to adjust the height of the perforated plate 46 relative to the cover 52.

Figure 2:
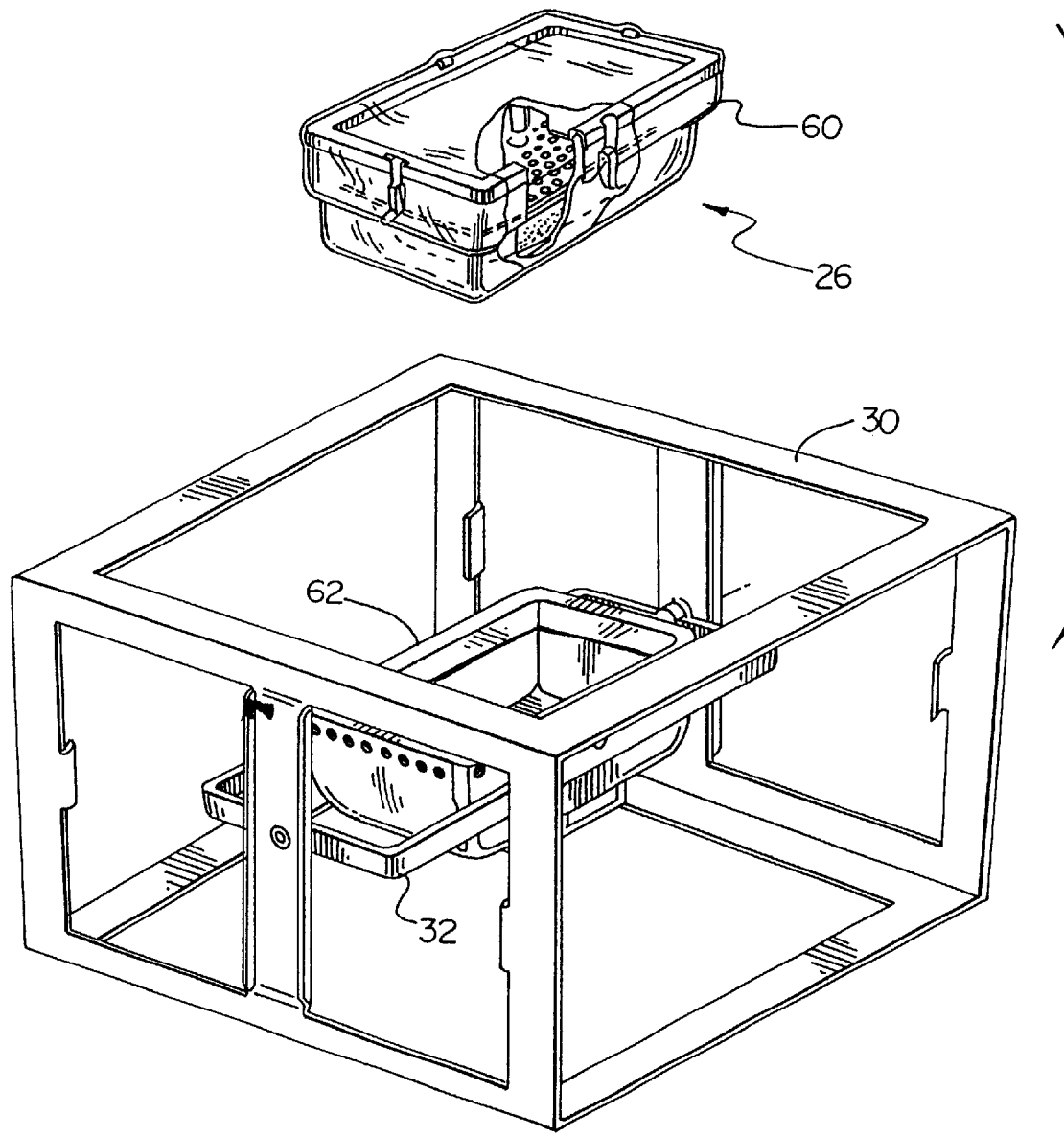
FIG. 2 is an exploded perspective view of the organ containment shipping system of the present invention with the main frame in a horizontal orientation.

The tray 50 and cover 52 are designed to be sterilized prior to each use. Because the tray 50 must be used within the sterile fields of two separate operating room environments, the tray 50 and cover 52 are preferably bagged in a sterile bag 60 as best shown in FIG. 2. In the sterile field of the initial operating room where the organ is removed, the organ is placed inside the tray 50 in a bottom layer 28b of the preservation medium 28. The top layer 28a of the preservation medium 28 is then carefully introduced above the bottom layer 28b. The bottom layer 28b of the preservation medium 28 is preferably a high oxygen carrier perflourochemical (PFC) liquid with the top layer 28b being a Euro-Collins (EC) solution. The cover 52 is attached to the tray 50 and the level of the bottom layer 28b of the preservation medium 28 is adjusted via the inlet port 40. The inlet port 40 and outlet port 42 are then sealed with rubber caps and the assembled inner container 26 is placed in a sterile bag 60.

Referring again to FIG. 13, a boundary level 29 between the bottom layer 28b of the preservation medium 28 and the top layer 28a of the preservation medium 28 is controlled by introducing or removing bottom PFC layer through the inlet port 40. This is desirable primarily because the level of the bottom PFC layer 28b is important in establishing and maintaining the best preservation medium for the organ, and in part because the bottom PFC layer 28b of the preservation medium 28 is a relatively expensive substance. The ability to accurately control this boundary level results in better oxygenation of the organ and can potentially decrease the amount of PFC bottom layer medium that is required, thereby reducing the overall cost of utilizing the dual layer preservation medium.

The assembled inner container 26 and the sterile bag 60 are then placed in the containment shipping system 20 outside of the sterile field as shown in FIG. 2. In this way, the remainder of the containment shipping system 20 does not need to be sterilized. After the shipping system 20 has been transported to be operating room where the organ will be transplanted, the assembled inner container 26 and the bag 60 are removed from the containment shipping system 20 outside of the sterile field. The inner container 26 is removed from the bag 60 and brought into the sterile field of the operating room where the organ will be transplanted. In this way, the inner container 26 and the bag 60 serve the same function as the conventional technique of double bagging an organ that is to be shipped for transplantation.

In a preferred embodiment, the secondary gimbal frame 32 is rotatably attached to a receptacle structure 62. The receptacle structure 62 is designed to allow the inner container 26 to be positioned in the containment shipping system 20 without the need for any mechanical attachments connections. Alternatively, the secondary gimbal frame 32 could be rotatably attached directly to the inner container 26; or latches or other similar mechanisms for securing the inner container 26 within the secondary gimbal frame 32 could be used. In this embodiment, the receptacle structure 62 not only receives the inner container 26, but also provides the mechanisms for maintaining and regulating the temperature of the inner container 26. An electronic module 64 is mounted on the bottom of the structure 62 and includes circuitry and batteries that are connected to a pair of fans 66 mounted in the side walls the structure 62. The fans 66 circulate air between the inner container 26 and the cool packs 24 to maintain a regulated temperature of the organ relative to the temperature of the cool packs 24.

In a preferred embodiment, the receptacle structure 62 is arranged with walls that define an enclosed space around the bottom portion of the inner container 26. A nesting collar 68 surrounds the top periphery of the receptacle structure 62. The nesting collar 68 supports the collar 58 around the tray 50 so as to hold the walls of the tray 50 in a spaced apart relation from the walls of the receptacle structure 62. In one embodiment, the distance of this spaced apart relation is generally defined by a depth of a U-shaped cross-section of the channel forming the nesting collar 68. Alternatively, the spaced apart relation could be defined by structure on the collar 58, or by a combination of these two collars. It should be understood that the collar structure 58 may be defined as part of the cover 52, rather than as part of the tray 50. In another embodiment, the bottom of the tray 50 is designed to be placed on the bottom of the receptacle structure 62 such that thermal transfer can also occur between these structures.

Figure 3:
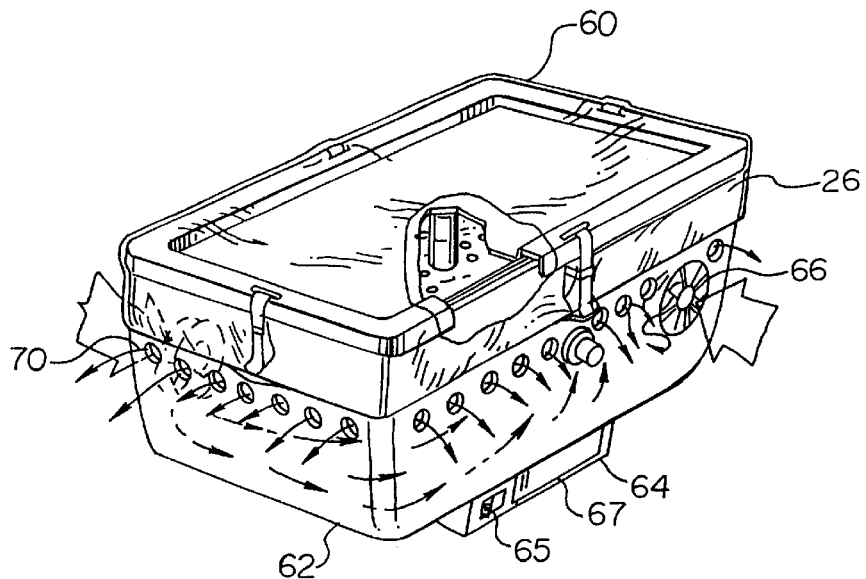
FIG. 3 is a perspective view of the assembled inner container and preferred embodiment of the receptacle structure showing air circulation.

Preferably, there are a plurality of apertures 70 in the outer walls of the receptacle structure 62 that form the U-shaped cross-section of the channel of the nesting collar 68. As shown in FIG. 3, air is drawn into the enclosed space between the tray 50 and receptacle structure 62 by the fans 66 and then exits from this space via the apertures 70. The U-shaped cross-section of the channel of the nesting collar 68 prevents the bag 60 from blocking the apertures 70, thereby allowing for effective air circulation within the enclosed space between the receptacle structure 62 and the inner container 26 even though the inner container 26 is contained within a flexible bag 60. In this embodiment, it is desirable for the flexible bag 60 to fit as snugly as possible against the inner container 26. It will also be understood that a double bag arrangement may be used with the present invention, or that the mainframe and 30 and outer container 22 could also be sterilized to allow the entire shipping containment system 20 to be brought within the sterile field of the first operating room.

Figure 5:
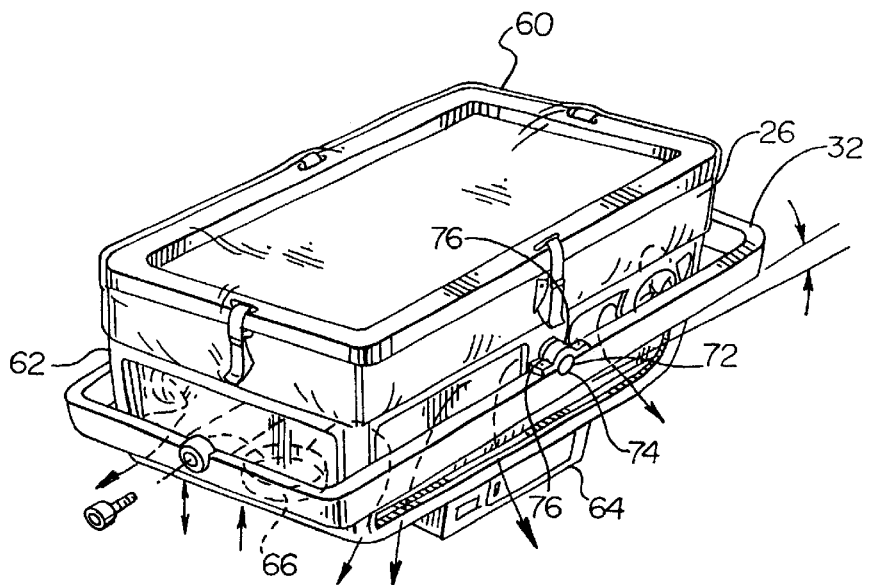
FIG. 5 is a perspective view of the inner container and receptacle structure mounted within the inner frame.
Figure 8:
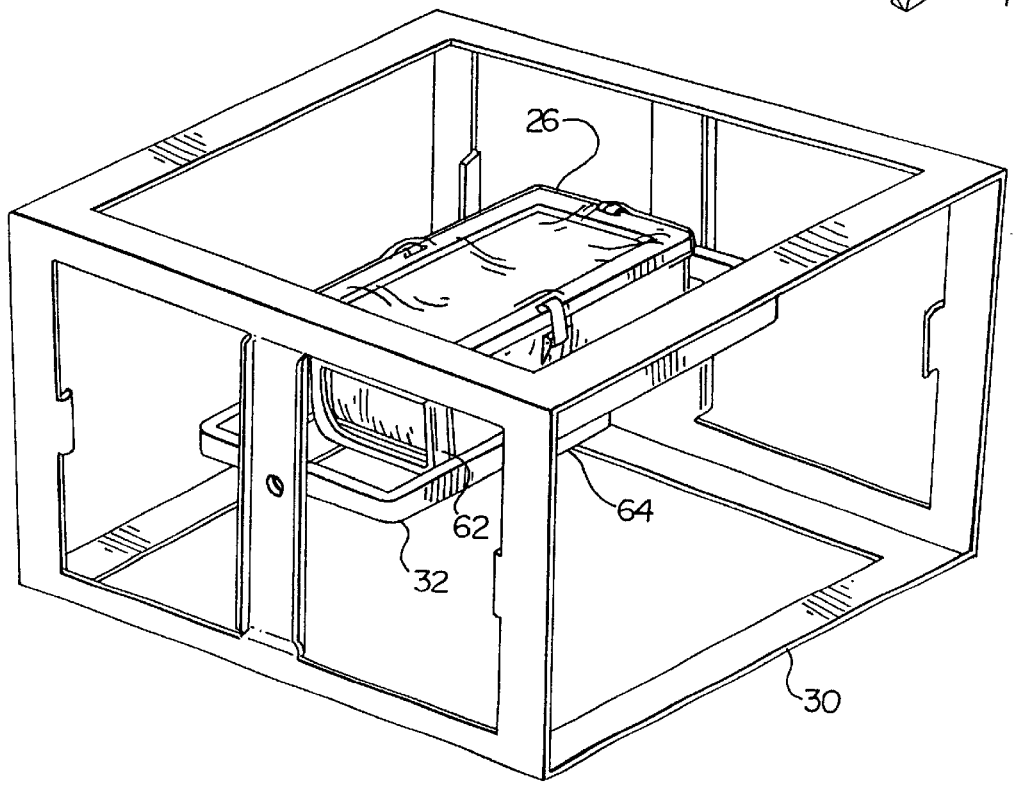
FIG. 8 is a perspective view of an alternate embodiment of the receptacle structure.

In an alternate embodiment as shown in FIGS. 5 and 8, the receptacle structure 62 comprises an open frame structure with the electronic module 64 and the fans 66 both mounted on the bottom of this frame. In this embodiment, the fans 66 direct air circulation up and around the inner container 26, although there is no defined enclosed space around the inner container 26 for this air circulation. Preferably, the housing enclosing the fans 66 includes a mesh or other structure to prevent the bag 60 from becoming in tangled with the fans 66 when the inner container 26 is in position in the receptacle structure 62.

In another embodiment, the receptacle structure 62 would comprise a completely enclosed metal frame with no apertures. The tray 52 inside the bag 60 would be designed to seat snuggly into the receptacle structure 62 to accommodate a direct thermal transfer from the metal of the receptacle structure 62 through the bag 60 to the tray 52. In this embodiment, the fans 66 could be mounted to the secondary gimbal frame 32 to blow cool air onto outer surface of the receptacle structure 62. Cooling fins or the like could also be used to further enhance the cooling effect of this embodiment.

In one embodiment, the electronic module 64 includes a simple analog circuit with one or more temperature sensors or thermistors that activate the fans 66 when the temperature rises above a first predetermined level and shut the fans 66 off when the temperature falls below a second predetermined level. It is preferably that there are more than one separately operable units for the fans 66 in order to provide redundancy in the event of the failure of one of these units. A shown in FIG. 3, a switch 65 is preferably provided to turn on the electronic module 64 as the time that the inner container 26 is inserted into the outer container 22. In another embodiment, electronic module 64 is provided with digital circuitry connected to one or more temperature sensors to monitor the temperature and activate the fans 66 via microcode or software control. Alternatively, the digital circuitry could include a state machine to monitor the temperature sensors and take appropriate action. The digital circuitry may also include optional connections or communication links to transmit status and recorded data from the electronic module 64, or to transfer control signals or setup commands to the electronic module 64. Alternatively, the electronic module 64 may also communicate via wires or an infrared or RF communication link with an external control/status panel on the outside of the exterior container 22. It will be apparent that numerous configurations of the electronic module 64 are possible. For ease of service, the batteries 67 of the electronic module 64 are adapted to be plugged into a portion of the bottom of the receptacle structure 62. The batteries in the electronic module 64 may either be replaceable or rechargeable. Alternatively, the entire electronic module 64 may be plugged into the bottom of receptacle structure 62.

Figure 6:
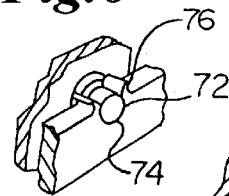
FIGS. 6 and 7 are detailed views of an alternate embodiment of the trunion assembly between the inner container and the inner frame.
Figure 7:
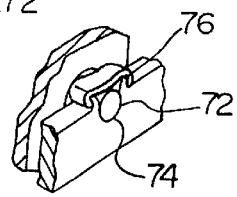

As shown in FIG. 1 and FIG. 5, the pair of second pivot assemblies 36 preferably includes a pair of gimbal trunions 72 mounted on opposite sides of the receptacle structure 62. The gimbal trunions 72 are positioned in a pair of corresponding secondary trunion seats 74 defined along the top edge of the secondary gimbal frame 32. A trunion clamp 76 secures the trunion 72 in the trunion seat 74 and is held in place by pair of screws 78. An alternate embodiment as shown in FIGS. 6–7, the trunion clamp 76 can be configured as a clip attaching to protrusions on the secondary gimbal frame 32 adjacent the secondary trunion seats 74. The pair of first pivot assemblies 34 preferably includes a pair of threaded primary gimbal trunions 80 that are mounted in a corresponding pair of primary trunion bores 82 defined in cross members of the main gimbal frame 30. The primary gimbal trunions 80 extend into a pair of primary trunion bores 84 defined in the secondary gimbal frame 32 on opposite sides from the secondary trunion seats 74. Preferably, a set screw 86 is used to secure the primary gimbal trunions 80 within the primary trunion bore 84 of the secondary gimbal frame 32. Although the preferred embodiment of the structure for maintaining the orientation of the inner container 26 relative to the outer container 22 is a gimbal mechanism, it will be recognized that other orientation mechanisms such as gyroscopes, cooperating slide rails, fluid leveling mechanisms, or even computer controlled stepper motors could also be used to accomplish this function.

Figure 4:
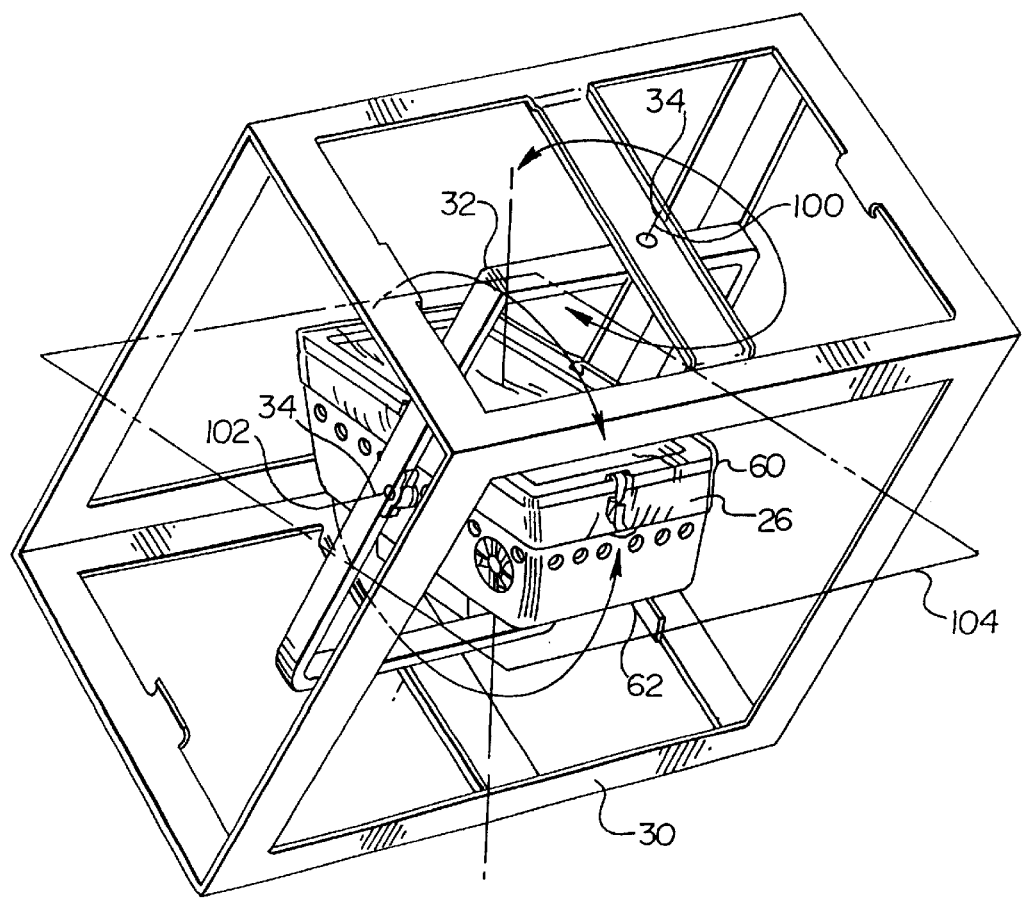
FIG. 4 is a perspective view showing the rotation of the inner container within the main frame.

Preferably, the inner container 26 is assembled and placed in bag 60 as shown in FIG. 2. This combination is then lowered into position in the container structure 62, with the primary gimbal frame 30 oriented in a horizontal position for optimal stability. Once in position, the inner container 26 is free to rotate about the primary gimbal axis 100 and the secondary gimbal axis 102 in response to any change in the orientation of the main frame 30 as shown in FIG. 4. It will be seen that because the main frame 30 is positioned within the outer container 22, the orientation of the outer container 22 and the main frame 30 is identical. The end result is that a horizontal plane 104 defined through the inner container 26 remains generally horizontal regardless of the orientation of the outer container 22 and the main frame 30. Because a horizontal plane 104 corresponds generally to the orientation of the perforated plate 46 retaining the organ in position within the inner container 26, the organ and the level of the dual layer preservation medium 28 are also maintained in a generally horizontal orientation. In the preferred embodiment, the ability of the gimbal mechanism to maintain the inner container 26 in an upright orientation regardless of the orientation of the outer container 22 is enhanced by locating the electronic module 64 on the bottom of the inner container 26 so as to act as a balance weight.

Figure 10:
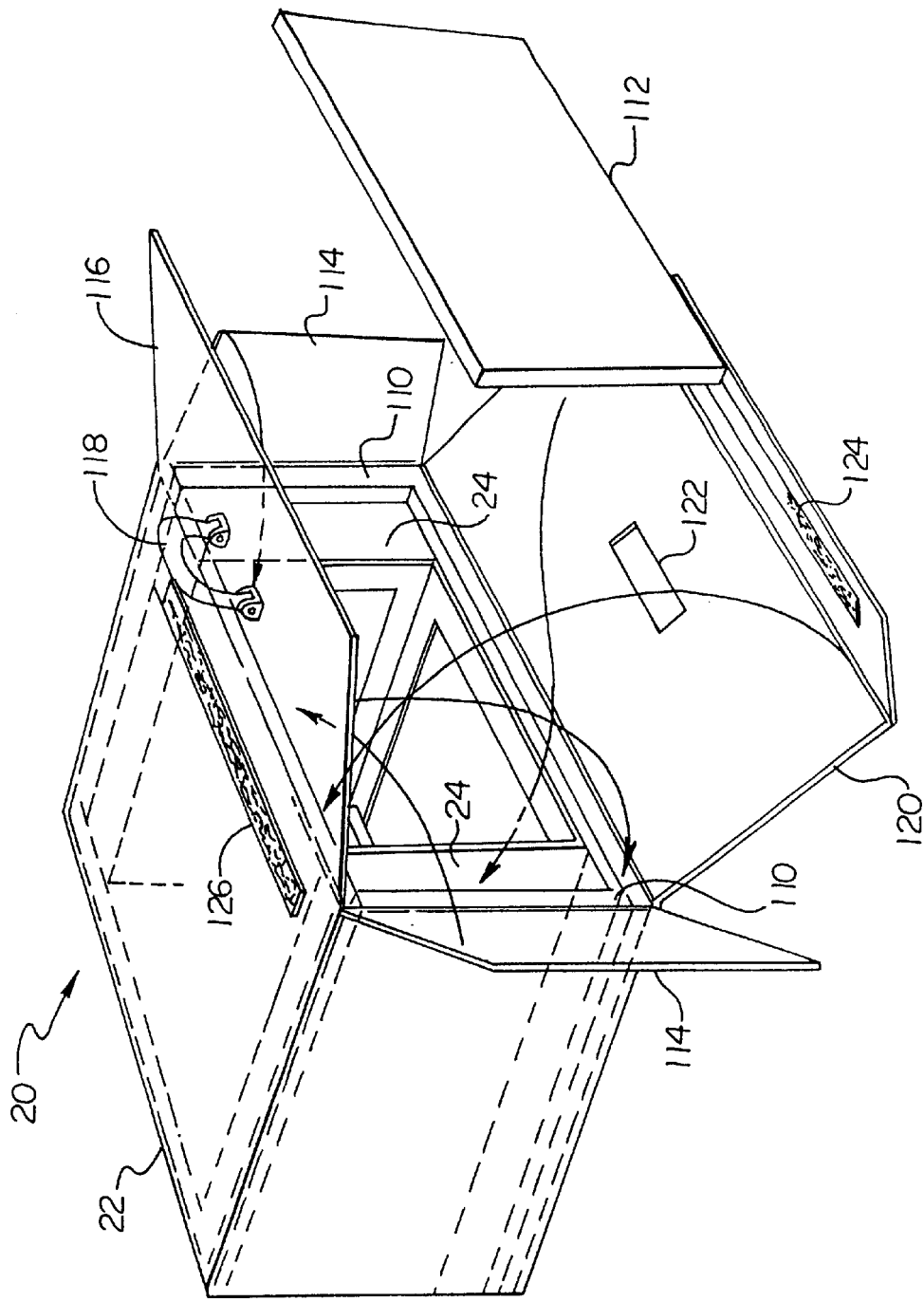
FIG. 10 is a perspective view showing the assembled main frame in the outer container.

Referring to FIGS. 9–10, the manner in which the inner container 26 is assembled in the outer container 22 will be described. For ease of understanding, the sterile bag 60 is not shown in these figures. Prior to inserting the inner container 26 and main frame 30 in the outer container 22 as shown in FIG. 9. the cool packs 24 are located along the sides of the opening of the outer container 22. Preferably, the cool packs 24 are self-contained passive chemical cool packs designed to maintain allow the system 20 to maintain the organ at a desired temperature. Preferably, the desired temperature for the organ in the preferred dual layer preservation medium would be between about 0–10 degrees Celsius, and optimally between about 4–8 degrees Celsius.

In this embodiment, the outer container 22 may be an insulated cardboard box with insulation panels 110 disposed along each side of the cardboard box. The cool packs 24 may also be located on the other sides of the container 22 or the top and bottom of the outer container 22, or any combination thereof. Alternatively, the outer container 22 may be a plastic or metal ice chest with the cool packs 24 replaced by crushed ice, ice packs or other similar passive cooling arrangements.

Figure 11:
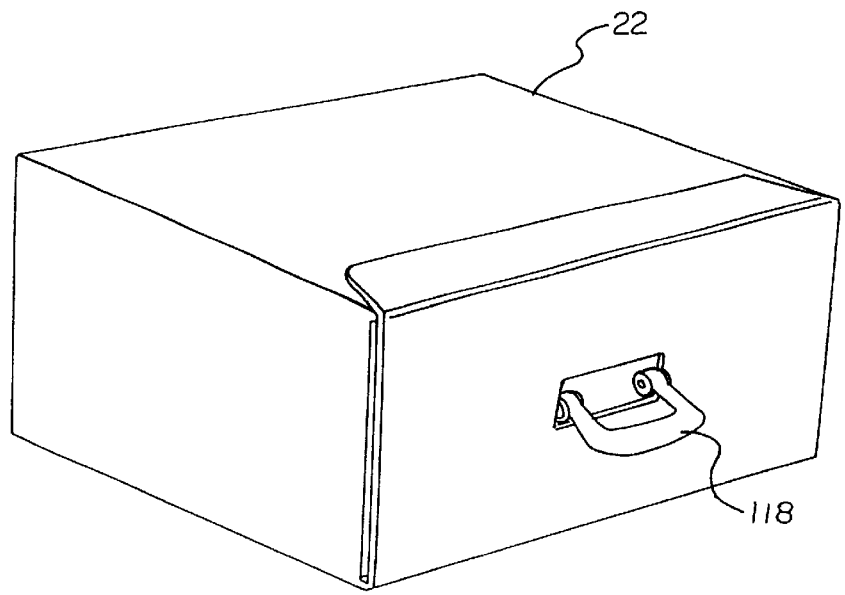
FIGS. 11 and 12 are perspective views of the assembled outer container in a horizontal and vertical orientation.
Figure 12:
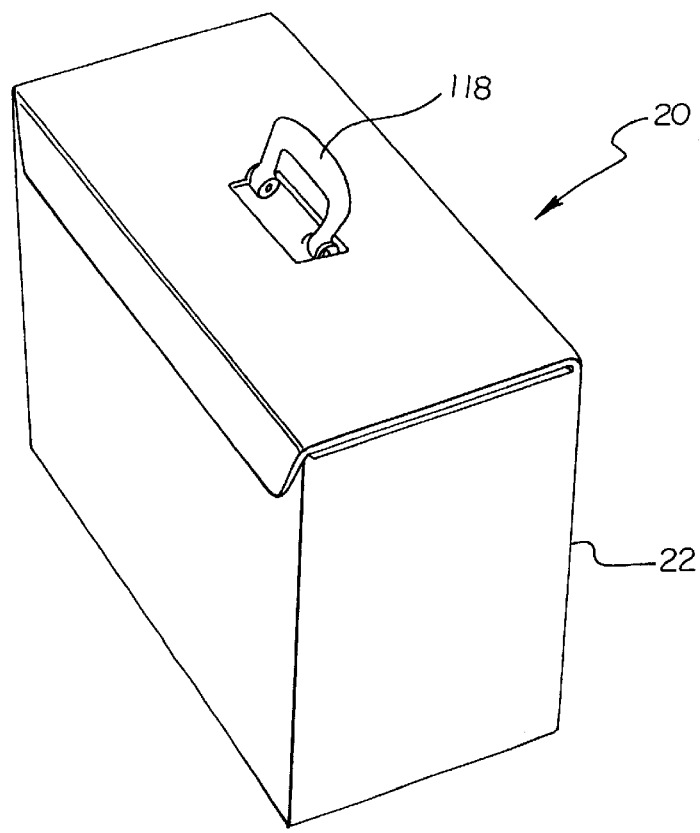

The inner container 26 and main frame 30 are slid into the outer container 22 preferably in a horizontal orientation. Once in position, a top insulation panel 112 is placed into the outer container 22 and side flaps 114 are closed. A first flap 116 having a handle 118 positioned in the center thereof is closed over the side flaps 114. A second flap 120 having an aperture 122 through which the handle 118 will extend is closed over the first flap 116 and secured. In the preferred embodiment, a first strip of Velcro material 124 on the second flap 120 latches to a second strip of Velcro material 126 on an outer side of the outer container 22. It will be recognized that other mechanisms for securing the flaps of the outer container 22 may be utilized such as latches, buckles or straps. Alternatively, the outer container 22 may be provided with a lockable latching system to prevent unauthorized access to the contents. FIGS. 11 and 12 show the organ containment shipping system 20 of the present invention as completely assembled in a horizontal and vertical orientation, respectively.

In the preferred embodiment, the inner container 26 is dimensioned in a rectangular arrangement having one pair of sides longer than the other pair of sides as shown in FIG. 3. The length of the shorter sides preferably ranges from 10 to 20 cm and a length of longer sides preferably ranges from 15 to 30 cm. The depth of the inner container 26 preferably ranges from 10 to 20 cm. An inner container 26 having these dimensions is generally large enough to accommodate a variety of organs, such as the pancreas, kidney, liver or heart. Alternatively, the inner container 26 may have larger dimensions or different shapes to accommodate different organs such as the lungs. The dimensions of the preferred embodiment are chosen to allow the outer dimensions of the outer container 22 to be generally within the range that would allow the outer container 22 to be carried onto an airline as carry on luggage. In this way, the organ containment shipping system 20 can be carried like a conventional briefcase in a vertical orientation as shown in FIG. 12 from the operating room to the airport. Once at the airport, the organ containment shipping system 20 can be positioned in a horizontal orientation as shown in FIG. 11 so as to allow it to be placed, for example, in an overhead compartment bin of a standard commercial airliner.

Although the preferred embodiment of the automated system of the present invention has been described, it will be recognized that numerous changes and variations can be made and that the scope of the present invention is to be defined by the claims.

What is claimed is:

1. An organ containment shipping system comprising:
   an outer container adapted to receive a passive cooling medium;
   an inner container adapted to receive an organ to be transported in a preservation medium; and
   structure to position the inner container within the outer container, the structure comprising:
   a main gimbal frame having a first pair of pivot assemblies;
   an inner gimbal frame having a second pair of pivot assemblies, the inner gimbal frame being connected to the main gimbal frame via the first pair of pivot assemblies and operably connected to the inner container via the second pair of pivot assemblies.

2. The system of claim 1 further comprising a receptacle structure rotatably attached to the second pair of pivot assemblies and adapted to receive the inner container therein.

3. The system of claim 2 wherein the receptacle structure further comprises:
  an electronic module operably mounted on a bottom of the receptacle structure and including circuitry and at least one battery; and
  at least one fan operably mounted on a side of the receptacle structure and electrically connected to the electronic module,
  such that the fans are selectively activated by the electronic module to circulate air between the inner container and the passive cooling medium to maintain a regulated temperature of the organ relative to a temperature of the passive cooling medium.

4. The system of claim 2 wherein the receptacle structure includes at least three walls that define an enclosed space around a bottom portion of the inner container and a nesting structure defined around at least a portion of a top periphery of the receptacle structure to support a tray and hold the tray in a spaced apart relation from the walls of the receptacle structure.

5. The system of claim 4 wherein the inner container nesting structure is a collar formed as a U-shaped cross-section channel along the top periphery of the receptacle structure and the spaced apart relation is generally defined by a depth of the U-shaped cross-section of the channel forming the nesting collar and wherein a plurality of apertures are defined in an outer wall of the channel to permit air circulation in a space defined by the spaced apart relation between the inner container and the receptacle structure.

6. An organ containment shipping system comprising:
  an outer container adapted to receive a passive cooling medium;
  an inner container adapted to receive an organ to be transported in a dual-layer preservation liquid; and
  structure to position the inner container within the outer container, the structure including a gimbal mechanism that substantially maintains the inner container in a predefined orientation in the event of a change of orientation of the outer container.

7. An organ containment shipping system comprising:
  an outer container adapted to receive a passive cooling medium;
  an inner container adapted to receive an organ to be transported in a preservation medium,
  wherein the inner container includes a perforated plate operably positioned therein to prevent the organ from rising in the preservation medium above a certain level; and
  structure to position the inner container within the outer container, the structure including a gimbal mechanism that substantially maintains the inner container in a predefined orientation in the event of a change of orientation of the outer container.

8. The system of claim 7 wherein the inner container comprises:
  a tray;
  a cover releasably attached to the tray; and
  a standoff structure operably connected to the cover on one end and to the perforated plate on the other end.

9. An organ containment shipping system comprising:
  an outer container adapted to receive a passive cooling medium,
  wherein the outer container comprises an insulated cardboard box with insulation panels disposed along each side of the cardboard box and having a handle arrangement on one side of the box;
  an inner container adapted to receive an organ to be transported in a preservation medium; and
  structure to position the inner container within the outer container, the structure including a gimbal mechanism that substantially maintains the inner container in a predefined orientation in the event of a change of orientation of the outer container.

10. The system of claim 9 wherein the passive cooling medium comprises at least one self-contained cool pack.

11. A regulated organ containment shipping system comprising:
  an outer container adapted to receive a passive cooling medium;
  an inner container adapted to receive an organ to be transported in a dual-layer preservation liquid having a bottom oxygen carrying layer and a top layer and wherein the inner container includes a perforated plate positioned in the inner container above a level of the bottom layer to prevent the organ from rising in the preservation medium;
  means for regulating a level of the preservation medium relative to the organ; and
  means for regulating a temperature of the organ relative to the cooling medium.

12. The system of claim 11 wherein the means for regulating the level of the preservation medium comprises:
  an inlet port having an inlet tube extending into the inner container below the perforated plate; and
  an outlet port defined in a top of the inner container
  such that the level of the bottom layer can be adjusted by introducing or withdrawing fluid for the bottom layer through the inlet port.

13. The system of claim 12 wherein means for regulating the level of the preservation medium further comprises a gimbal mechanism that substantially maintains the inner container in a predefined orientation in the event of a change of orientation of the outer container.

14. A regulated organ containment shipping system comprising:
  an outer container adapted to receive a passive cooling medium;
  an inner container adapted to receive an organ to be transported in a preservation medium;
  means for regulating a level of the preservation medium relative to the organ; and
  means for regulating a temperature of the organ relative to the cooling medium, wherein means for regulating the temperature of the organ relative to the passive cooling medium comprises at least one fan operably connected to an electronic module housing at least one battery and circuitry connected to at least one sensor that activates the at least one fan when the at least one sensor indicates that the temperature has risen above a first predetermined level and deactivates the at least one fan when the at least one sensor indicates that the temperature has fallen below a second predetermined level.

* * * * *